US008658226B2

(12) United States Patent
Sato et al.

(10) Patent No.: US 8,658,226 B2
(45) Date of Patent: Feb. 25, 2014

(54) **AGENT HAVING ANTI-*HELICOBACTER PYLORI* ACTIVITY**

(75) Inventors: Yoshiya Sato, Okinawa (JP); Hiromu Toma, Okinawa (JP); Hironori Iwasaki, Okinawa (JP); Kikuji Yamaguchi, Shizuoka (JP)

(73) Assignees: Japan Royal Jelly Co., Ltd., Tokyo (JP); University of the Ryukyus, Atami-Shi (JP)

( * ) Notice: Subject to any disclaimer, the term of this patent is extended or adjusted under 35 U.S.C. 154(b) by 210 days.

(21) Appl. No.: 13/126,770

(22) PCT Filed: Oct. 30, 2009

(86) PCT No.: PCT/JP2009/068668
§ 371 (c)(1),
(2), (4) Date: Apr. 29, 2011

(87) PCT Pub. No.: WO2010/050583
PCT Pub. Date: May 6, 2010

(65) Prior Publication Data
US 2011/0206791 A1 Aug. 25, 2011

(30) Foreign Application Priority Data
Oct. 30, 2008 (JP) .................................. 2008-279358

(51) Int. Cl.
*A61K 36/53* (2006.01)
*A61K 36/00* (2006.01)

(52) U.S. Cl.
USPC ............................ 424/745; 424/725; 424/778

(58) Field of Classification Search
None
See application file for complete search history.

(56) References Cited

U.S. PATENT DOCUMENTS

| | | | | |
|---|---|---|---|---|
| 4,419,349 | A * | 12/1983 | Kojima et al. | 424/745 |
| 5,882,664 | A * | 3/1999 | Soma et al. | 424/745 |
| 2010/0021582 | A1 * | 1/2010 | Kwon | 426/11 |
| 2010/0129462 | A1 | 5/2010 | Yamaguchi et al. | |
| 2010/0178409 | A1 * | 7/2010 | Kashima | 426/538 |

FOREIGN PATENT DOCUMENTS

| | | | |
|---|---|---|---|
| JP | 59078646 | * | 5/1984 |
| JP | 60237961 | * | 11/1985 |
| JP | 63207360 | * | 8/1988 |
| JP | 04158737 | * | 6/1992 |
| JP | 06133744 | * | 5/1994 |
| JP | 07196522 | * | 8/1995 |
| JP | 08295632 | * | 11/1996 |
| JP | 11-5745 A | | 1/1999 |
| JP | 11075790 | * | 3/1999 |
| JP | 2001-270835 A | | 10/2001 |
| JP | 2002262811 | * | 9/2002 |
| JP | 2003206238 | * | 7/2003 |
| JP | 2003-252776 A | | 9/2003 |
| JP | 2006223143 | * | 8/2006 |
| KR | 2003095540 | * | 12/2003 |
| WO | WO 2008/133098 A1 | | 11/2008 |

OTHER PUBLICATIONS

Banno et al. Biosci. Biotechnol. Biochem. 2004. vol. 68, No. 1, pp. 85-90.*
International Preliminary Report on Patentability issued Jun. 16, 2011, in PCT International Application No. PCT/JP2009/068668.
International Search Report, dated Jan. 19, 2010, issued in PCT/JP2009/068668.
"How to make everyday snacks handily 260," ed. Luo Fuxiang, Guangxi Race Publishing Company, 1st ed., pp. 71-72, Apr. 30, 1992.
Hu et al., "Study on extraction and antibacterial and activity of active constituents of *Elshoitzia ciliata* Hyland" Pratacultural Science (Aug. 2007), vol. 24, No. 8, pp. 36-39, with English abstract.
La I et al., "Chemical constituents from *Elsholtzia rugulosa*," Chinese Traditional and Herbal Drugs (2008), vol. 39, No. 5, pp. 661-684, with English abstract.
Office Action issued Mar. 1, 2012, in Chinese Patent Application No. 200980143318.2, with English translation.

* cited by examiner

*Primary Examiner* — Chris R Tate
(74) *Attorney, Agent, or Firm* — Birch, Stewart, Kolasch & Birch, LLP

(57) ABSTRACT

The present invention provides an agent having anti-*Helicobacter pylori* activity that is effective for the treatment, prevention or improvement of diseases associated with *Helicobacter pylori* and contains as an active ingredient thereof an extract of a plant belonging to the Labiatae family. The agent having anti-*Helicobacter pylori* activity of the present invention has superior heat stability and allows the obtaining of elimination effects in a short period of time.

9 Claims, No Drawings

AGENT HAVING ANTI-*HELICOBACTER PYLORI* ACTIVITY

TECHNICAL FIELD

The present invention relates to an agent having anti-*Helicobacter pylori* activity capable of effectively eliminating and discharging *Helicobacter pylori* involved in the onset of peptic ulcers.

BACKGROUND ART

*Helicobacter pylori* (hereinafter also referred to as *H.pylori*) is a Gram-negative rod (spirochete) that has several polar flagella. These organisms were named Helicobacter (bacteria that spiral) since they move by rotating these flagella. In addition, they are also characterized by being able to survive in the strongly acidic environment of the human stomach, and primarily infect the pylorus as is indicated by their name, pylori.

Human infection is thought to occur by oral infection. In the case of Japanese, infection through one-time well water is presumed to be the main infection route. Consequently, although infection is rare among young persons who grew up in an age of advanced water utility facilities, middle-aged to elderly persons older than age 50 have conversely been indicated as demonstrating as high infection rate of greater than 70%.

Warren and Marshall first detected and isolated *H.pylori* from gastritis patients in 1982. As a result of subsequent infection experiments independently conducted by Marshall in 1984, *H.pylori* was verified to be directly involved in the onset of acute gastritis. Subsequently, *H.pylori* has been strongly indicated to be involved in the onset of atrophic gastritis, gastric and duodenal ulcers, gastric mucosa-associated lymphoid tissue (MALT) lymphoma, and gastric cancer. At present, patients infected with *H.pylori* are recommended to undergo elimination treatment regardless of the presence or absence of symptoms from the standpoint of preventing these diseases.

Although chemotherapy using antibiotics such as Clarithromycin or Amoxicillin is comparatively effective for treatment, approximately 20% of patients were said to be resistant to treatment due to infection by resistant strains. There is concern that the proportion of resistant strains will increase rapidly in the future. Moreover, administration of these conventional antibiotics is frequently associated with the problems regarding safety during long-term administration and recurrence, thus creating the need for the development of a drug that is both effective and safe.

DISCLOSURE OF THE INVENTION

The present invention provides an agent having anti-*Helicobacter pylori* activity that is useful for the treatment, prevention or improvement of diseases associated with *Helicobacter pylori*.

The inventors of the present invention found that an extract of a plant belonging to the Labiatae family is able to effectively inhibit growth of *Helicobacter pylori*, thereby leading to completion of the present invention.

Namely, the present invention relates to the following:
1. an agent having anti-*Helicobacter pylori* activity, which comprises as an active ingredient thereof an extract of a plant belonging to the Labiatae family;
2. the agent having anti-*Helicobacter pylori* activity according to 1 above, wherein the plant belonging to the Labiatae family is *Elsholtzia ciliata* or *Perilla frutescens viridis*;
3. the agent having anti-*Helicobacter pylori* activity according to 1 above, wherein the plant belonging to the Labiatae family is *Elsholtzia rugulosa*;
4. the agent having anti-*Helicobacter pylori* activity according to any of 1 to 3 above, wherein the extract contains a fraction that has been passed through a filter having a molecular weight cut-off of 5,000;
5. the agent having anti-*Helicobacter pylori* activity according to any of 1 to 4 above, which is used for the treatment, prevention or improvement of diseases associated with *Helicobacter pylori*;
6. a method for eliminating *Helicobacter pylori*, comprising consuming the agent having anti-*Helicobacter pylori* activity according to any of 1 to 5 above; and,
7. a food additive composition for eliminating *Helicobacter pylori* comprising an extract of a plant belonging to the Labiatae family.

The agent having anti-*Helicobacter pylori* activity of the present invention has superior growth inhibitory action, elimination action and discharge action on *Helicobacter pylori*, and is highly safe. In addition, the agent having anti-*Helicobacter pylori* activity of the present invention has superior heat stability. Moreover, the agent having anti-*Helicobacter pylori* activity of the present invention allows the obtaining of elimination effects in a short period of time. Thus, it is extremely useful for the elimination of *Helicobacter pylori*, and the treatment, prevention or improvement of diseases associated with *Helicobacter pylori*.

BEST MODE FOR CARRYING OUT THE INVENTION

In the present invention, the agent having anti-*Helicobacter pylori* activity refers to a composition that is able to inhibit growth of *Helicobacter pylori*. Such an agent having anti-*Helicobacter pylori* activity is able to eliminate *Helicobacter pylori* from the stomach. The agent having anti-*Helicobacter pylori* activity of the present invention can be used to treat, prevent or improve diseases associated with *Helicobacter pylori*, and more specifically, peptic ulcers such as gastric and duodenal ulcers, gastritis (including acute gastritis and atrophic gastritis), gastric MALT lymphoma and gastric cancer, etc.

In the present invention, any arbitrary plant can be used for the plant belonging to the Labiatae family provided it is a plant that belongs to the Labiatae family, and a plant belonging to the genus *Elsholtzia* is preferable, and *Elsholtzia ciliata*, *Perilla frutescens viridis* or *Elsholtzia rugulosa* is more preferable. *Elsholtzia ciliata* is used as a Chinese herbal medicine. *Perilla frutescens viridis* is also widely available for edible purposes. *Elsholtzia rugulosa* is commonly used as a tea in China. Thus, extracts thereof are highly safe and can be used continuously for a long period of time.

Dried one of plants belonging to the Labiatae family such as *Elsholtzia ciliata* or *Perilla frutescens viridis* are available commercially, and these can also be used in the present invention. *Elsholtzia rugulosa* growing wild in the Yunnnan Province of China can be used for the *Elsholtzia rugulosa* in the present invention. In addition, the plant belonging to the Labiatae family used in the present invention may be in a raw form or dried form following collection. Examples of collected sites include mature or immature spikes, fruit, skin, seeds, leaves, leaf stems, branches and roots. Spikes are used preferably.

Extraction can be carried out by a commonly used extraction method such as extracting an active ingredient from a plant raw material with an extraction solvent. Extraction may also be carried out after crushing the plant raw material. A commonly used method can be applied for the crushing method, such as crushing using a mortar and pestle, atomizer, hammer mill, stamp mill or ball mill, etc.

Examples of extraction solvents include water; alcohols such as methanol, ethanol, isopropanol, t-butanol, octanol or 2-methyl-4-phenylbutanol; ketones such as acetone, methyl isobutyl ketone, acetophenone or benzophenone; esters such as ethyl acetate, butyl acetate, methyl benzoate or t-butyl benzoate, hydrocarbons such as hexane, heptane, octane, decane, undecane, dodecane, cyclohexane or decalin, buffer solutions such as phosphate-buffered saline (PBS); and mixtures thereof. Preferable examples include water, methanol, ethanol, hexane, ethyl acetate, acetone, phosphate-buffered saline (PBS) and mixtures thereof. Mixed solvents of water and a hydrophilic solvent can also be used for the extraction solvent. The ratio between the water and hydrophilic solvent can be suitably determined over a wide range, and the ratio of water to hydrophilic solvent is, for example, 95:5 to 5:95 and preferably 50:50 to 10:90. For example, 50% aqueous ethanol solution can be used.

Extraction is carried out by, for example, using 0.1 to 10000 parts by weight, and preferably 1 to 100 parts by weight of solvent to 1 part by weight of plant body. There are no particular limitations on extraction temperature, and the extraction temperature is, for example, preferably 0 to 100° C. and more preferably 20 to 90° C. There are no particular limitations on extraction time, and the extraction time is, for example, preferably 1 minute to 1 week and more preferably 30 minutes to 1 day.

There are no particular limitations on the equipment used for extraction, and examples of equipment include a container, stirrer, reflux condenser, Soxhlet extractor, homogenizer, shaker and ultrasonic generator designed for efficient extraction.

An extract can be treated with various types of solid-liquid separation methods such as sedimentation separation, cake filtration, supernatant filtration, clarifying filtration, centrifugal filtration, centrifugal sedimentation, expression separation or the use of a filter press.

An extract may be used after passing through a filter having a molecular weight cut-off of a certain value. A fraction obtained by passing through a filter having a molecular weight cut-off of 20,000 can be used preferably, and a fraction obtained by passing through a filter having a molecular weight cut-off of 5,000 can be used more preferably.

An extract extracted with an extraction solvent may be used as is, or may be used after diluting or concentrating. Alternatively, the extract may be powdered by a method such as freeze-drying or spray-drying.

In addition, in the agent having anti-*Helicobacter pylori* activity of the present invention, the amount of extract used may be an amount that is effective for expression of antibacterial activity against *Helicobacter pylori*, and is, for example, about 0.01 to 10.0 g as extract or about 0.1 mg to 5.0 g as dried extract per dosage unit or per day in adults. Normally, the concentration of an extract in a preparation varies according to the form thereof, and in the case of a solid form such as tablets, chewable tablets, granules or capsules (e.g., hard capsules), the amount of extract used is within the range of 0.01 to 100% by weight and preferably 10 to 100% by weight based on total weight of the preparation. The preparation is preferably prepared so that the final concentration of active ingredient in the stomach is 10 to 100 µg/ml.

Examples of forms of the agent having anti-*Helicobacter pylori* activity of the present invention include various forms of solid foods and liquid foods such as tablets, chewable tablets, granules or capsules (e.g., hard capsules), liquid beverages and foods such as soups, juices, tea drinks, milk drinks, fermented milk drinks, soy milk, cocoa drinks and jellied drinks, semi-solid foods such as pudding or yogurt, breads, noodles such as udon, confections such as cookies, chocolate, candy or crackers, and spreads such as rice seasonings, butter or jam, and the like. In addition, the agent having anti-*Helicobacter pylori* activity of the present invention can also be in the form of a health food or therapeutic food. There are no particular limitations on the form thereof, and preferable examples include a form that enables continuous ingestion, such as tablets, chewable tablets, granules or capsules (e.g., hard capsules) as well as confections, soups, beverages and liquid foods.

Moreover, the agent having anti-*Helicobacter pylori* activity of the present invention can incorporate various food additives, examples of which include various types of nutrients, various vitamins, minerals, dietary fiber, polyunsaturated fatty acids, stabilizers such as dispersants or emulsifiers, sweeteners, taste components and flavorings. In addition, in the case of liquids, the agent having anti-*Helicobacter pylori* activity of the present invention may be initially prepared in the form of a liquid, and it may also be prepared in the form of a powder or paste followed by dissolving in a prescribed amount of an aqueous liquid.

The agent having anti-*Helicobacter pylori* activity of the present invention can also be used by adding to an arbitrary food material such as milk, fruit juice such as orange or lemon juice, dairy products such as yogurt, bread or other foods.

The agent having anti-*Helicobacter pylori* activity of the present invention has superior heat stability. Thus, activity can be maintained even in cases where the agent is added to the aforementioned foods and heated.

Since the agent having anti-*Helicobacter pylori* activity of the present invention is able to eliminate *Helicobacter pylori* present in the gastrointestinal tract, it can be used to treat, prevent or improve diseases associated with *Helicobacter pylori*. Examples of diseases associated with *Helicobacter pylori* include diseases caused by the presence of *Helicobacter pylori* in the gastrointestinal tract. More specifically, examples of diseases associated with *Helicobacter pylori* include peptic ulcers such as gastric ulcers and duodenal ulcers, gastritis (including acute gastritis and atrophic gastritis), gastric MALT lymphoma and gastric cancer (Diagnosis and Treatment Guidelines for *Helicobacter pylori* Infection (Revised Edition), The Japanese Society for Helicobacter Research, 2003). The Japanese Society for Helicobacter Research has published "Diagnosis and Treatment Guidelines" in June 2000, and has proposed the indication of elimination treatment for all gastric ulcers and duodenal ulcers positive for *Helicobacter pylori*.

The following examples provide a more detailed explanation of the present invention, but the present invention is not limited thereto.

EXAMPLES

Example 1

Preparation of Extract

*Elsholtzia rugulosa*, *Elsholtzia ciliata* and *Perilla frutescens viridis* were used as plants belonging to the Labiatae family. Plant bodies (including spikes) collected in Daicho, Yunnan Province, China followed by drying were used for *Elsholtzia rugulosa*. A commercially available product obtained by cutting an entire dried plant obtained during the flowering season into strips was used for *Elsholtzia ciliata* (Hyakkaen Kampo Pharmacy, Neyagawa, Japan). Commercially available dried spikes and leaves were used for *Perilla frutescens viridis*.

Extraction was carried out by crushing the dried plant body with a mortar and pestle, and extracting overnight at 4° C. using 30 ml of extraction solvent to 1 g of the resulting dried powder. PBS, 50% ethanol and 100% ethanol were used for the extraction solvent. The resulting mixture was then centrifuged for 30 minutes at 4,000 rpm followed by collection of the resulting supernatant thereof. Samples obtained by the extraction with 50% ethanol or 100% ethanol was evaporated to remove alcohol, and the resulting dried powder of those samples were dissolved in a prescribed amount of PBS and then used after filtering with a Millipore membrane filter. The sample extract obtained by the extraction with PBS was used as is or after concentrating and filtering as necessary.

Test Example 1

Measurement of Anti-*Helicobacter pylori* Activity

Measurement of anti-*Helicobacter pylori* activity was carried out by the paper disk method using *Helicobacter pylori* agar culture medium (Pore Media Vi HELICO AGAR, Eiken Chemical). After coating *Helicobacter pylori* over the entire surface of this medium, a thick circular piece of filter paper (Advantec) having a diameter of 8 mm impermeated with 60 µl of extract was placed on the medium followed by culturing in the presence of 10% carbon dioxide gas. After culturing for 3 to 4 days, the size of the zone of inhibition of *Helicobacter pylori* growth formed around the filter paper was observed. A piece of filter paper impermeated with chloramphenicol (CM, 100 µg/ml) was also placed on the medium as a positive control, while a piece of filter paper impermeated with PBS was placed on the medium as a negative control.

Results:

(1) *Elsholtzia rugulosa* Extract

A PBS extract of *Elsholtzia rugulosa* spikes was observed to have potent anti-*Helicobacter pylori* activity. Based on an evaluation of the size of zone of inhibition of *Helicobacter pylori* growth, the anti-*Helicobacter pylori* activity of *Elsholtzia rugulosa* spike extract was nearly equivalent to the activity at a concentration of 100 µg/ml of chloramphenicol. Antibacterial activity of chloramphenicol was essentially no longer observed at a concentration of 5 µg/ml. If the minimum inhibitory concentration (MIC) of chloramphenicol as determined according to this method is assumed to be about 5 µg/ml, then the minimum inhibitory concentration (MIC) of *Elsholtzia rugulosa* spike extract against *Helicobacter pylori* is 1/20 that of chloramphenicol, or 0.25 µg/ml.

Moreover, a 50% ethanol extract of *Elsholtzia rugulosa* spikes demonstrated anti-*Helicobacter pylori* activity that was more potent than that of the PBS extract. In addition, an extract obtained by extracting residue remaining after extracting *Elsholtzia rugulosa* spikes with PBS with 50% aqueous ethanol solution was observed to have even more potent anti-*Helicobacter pylori* activity.

(2) *Elsholtzia ciliata* Extract

A PBS extract of an entire *Elsholtzia ciliata* plant was confirmed to demonstrate definitive anti-*Helicobacter pylori* activity in a solution concentrated by a factor of 5. In addition, a 50% ethanol extract and 100% ethanol extract of an entire *Elsholtzia ciliata* plant demonstrated anti-*Helicobacter pylori* activities that were more potent than that of the PBS extract.

(3) *Perilla frutescens viridis* Extract

A PBS extract of spikes of *Perilla frutescens viridis* was observed to demonstrate potent anti-*Helicobacter pylori* activity without concentrating. The anti-*Helicobacter pylori* activity of this PBS extract of *Perilla frutescens viridis* spikes exceeded activity of chloramphenicol at a concentration of 100 µg/ml. In addition, a 50% ethanol extract of *Perilla frutescens viridis* spikes was observed to demonstrate anti-*Helicobacter pylori* activity that was equal to that of the PBS extract.

Test Example 2

Heat Stability of Anti-*Helicobacter pylori* Activity

In order to examine the heat stability of substances having anti-*Helicobacter pylori* activity, a PBS extract of *Elsholtzia rugulosa* spikes, a 50% ethanol extract of *Elsholtzia ciliata* and a PBS extract of *Perilla frutescens viridis* spikes were heat-treated (boiled) for 20 minutes at 100° C. followed by an examination of the anti-*Helicobacter pylori* activity thereof. Activity was measured using the same method as that of Example 1 above.

Results:

The heat-treated extracts maintained anti-*Helicobacter pylori* activity equal to that of extracts prior to heat treatment for all of the extracts examined.

Test Example 3

Study of Molecular Size of Substances Having Anti-*Helicobacter pylori* Activity A study was made of the molecular size of antibacterial substances contained in extracts. Using a PBS extract of *Elsholtzia rugulosa*, a 50% ethanol extract of *Elsholtzia ciliata* spikes and a PBS extract of *Perilla frutescens viridis*, each of the extracts were respectively passed through molecular weight cut-off filters having cut-offs of 30,000, 20,000, 10,000 and 5,000 followed by measurement of the antibacterial activity thereof Activity was measured using the same method as that of Example 1 above.

Results:

Potent anti-*Helicobacter pylori* activity was observed in fractions having a molecular weight of 5,000 or less for all of the extracts examined. Anti-*Helicobacter pylori* activity was not observed in the PBS extract of *Perilla frutescens viridis* in fractions having a molecular weight of more than 5,000.

Test Example 4

Determination of Anti-*Helicobacter pylori* Activity Ingredient of *Elsholtzia rugulosa*

Antibacterial substances were attempted to be isolated and purified using an extract obtained by extracting *Elsholtzia rugulosa* spikes with 100% methanol. First, after concentrating the 100% methanol extract of *Elsholtzia rugulosa* spikes, the concentrate was extracted with hexane, ethyl acetate and PBS, respectively using partition chromatography. Among the resulting extracts, potent antibacterial activity was observed for the hexane and ethyl acetate fractions. Next, the ethyl acetate fraction that demonstrated potent activity was applied to a silica gel cartridge column. Among fractions A1 to A10 extracted with a solution of chloroform and methanol (Fr. A1 to Fr. A10), antibacterial activity was observed in Fr. A5 and Fr. A10 (chloroform:methanol=4:1). These two fractions were then combined and further subjected to methanol extraction using an ODS cartridge column. A fraction B1 in which activity was observed (Fr. B1) was purified with a preparative HPLC column, and as a result of examining the resulting fractions C1 to C99 (Fr. C1 to Fr. C99), antibacterial activity was observed in Fr. C10 to Fr. C12. On the basis of these isolation and purification results, substances demonstrating anti-*Helicobacter pylori* activity were determined to be highly polar, hydrophobic substances that are easily extracted with organic solvents such as hexane and ethyl acetate.

INDUSTRIAL APPLICABILITY

As has been described above, the agent having anti-*Helicobacter pylori* activity of the present invention has superior growth inhibitory action, elimination action and discharge action on *Helicobacter pylori*, and has superior heat stability.

The invention claimed is:

1. A method for eliminating *Helicobacter pylori* (*H. pylori*) from the gastrointestinal tract of a subject infected with and/or harboring *H. pylori*, the method comprising orally administering a composition comprising an effective amount of an extract of *Pefilla frutescens* spikes to said subject.

2. The method according to claim 1, wherein the *Perilla frutescens* extract is a filtered extract that has been passed through a filter having a molecular weight cutoff of 5.000.

3. The method according to claim 1, wherein the *Perilla frutescens* is *Perilla frutescens viridis*.

4. The method according to claim 1, wherein the composition is in the form of a dosage unit and/or is orally administered on a daily basis, and wherein the extract is within a range of 0.01 to 10 grams per dosage unit or per daily administration.

5. The method according to claim 1, wherein the extract is in the form of a dried extract and wherein the subject is an adult subject.

6. The method according to claim 5, wherein the composition is in the form of a dosage unit and/or is orally administered on a daily basis to the adult subject, and wherein the dried extract is within a range of 0.01 to 5 grams per dosage unit or per daily administration.

7. The method according to claim 1, wherein the extract is present in a dosage form selected from the group consisting of a tablet, a chewable table, a granule, or a capsule.

8. The method according to claim 7, wherein the extract is present in an amount of 10% to 100% by weight based on the total weight of the dosage form.

9. A method for eliminating *H. pylori* from the gastrointestinal tract of a subject infected with and/or harboring *H. pylori*, the method comprising orally administering an effective amount of a composition consisting essentially of an extract of *Perilla frutescens* spikes to said subject.

* * * * *